United States Patent [19]
Audeh et al.

[11] Patent Number: 5,292,493
[45] Date of Patent: Mar. 8, 1994

[54] CLEAN UP OF ETHANOLAMINE SOLUTION BY TREATING WITH WEAK ION EXCHANGE RESINS

[75] Inventors: Costandi A. Audeh, Princeton, N.J.; Tsoung Y. Yan, Philadelphia, Pa.

[73] Assignee: Mobil Oil Corporation, Fairfax, Va.

[21] Appl. No.: 802,586

[22] Filed: Dec. 5, 1991

Related U.S. Application Data

[60] Continuation of Ser. No. 628,310, Dec. 17, 1990, abandoned, which is a continuation-in-part of Ser. No. 542,282, Jun. 22, 1990, abandoned, which is a continuation of Ser. No. 288,392, Dec. 22, 1988, abandoned, which is a division of Ser. No. 113,316, Oct. 28, 1987, Pat. No. 4,795,565.

[51] Int. Cl.$^5$ .................... C01B 17/16; C01B 31/20; C02F 1/42
[52] U.S. Cl. .................... 423/229; 210/681; 210/683; 210/685; 521/26
[58] Field of Search .............. 423/229; 54/26; 210/681, 683, 685

[56] References Cited

U.S. PATENT DOCUMENTS

| | | | |
|---|---|---|---|
| Re. 29,428 | 10/1977 | Homberg et al. | 423/228 |
| 2,797,188 | 6/1957 | Taylor, Jr. et al. | 423/229 |
| 4,477,419 | 10/1984 | Pearce et al. | 423/228 |
| 4,525,483 | 6/1985 | Grier et al. | 521/28 |
| 4,795,565 | 1/1989 | Yan | 423/228 |
| 4,820,421 | 4/1989 | Auerswald | 210/670 |
| 4,970,344 | 11/1990 | Keller | 423/229 |
| 5,045,291 | 9/1991 | Keller | 423/229 |

OTHER PUBLICATIONS

*Heat-Stable Salt Removal From Amines By The HSSX Process Using Ion Exchange* By: A. E. Keller et al., Presented Mar. 2, 1992 to The Laurence Reid Gas Conditioning Conference.

*Primary Examiner*—Thurman K. Page
*Assistant Examiner*—Peter F. Kulkosky
*Attorney, Agent, or Firm*—Alexander J. McKillop; Dennis P. Santini; Robert B. Furr, Jr.

[57] ABSTRACT

The present invention provides a process for removing heat stable salts which accumulate in alkanolamine gas purification process units. Surprisingly, it has been found that weakly acidic cationic exchange resins are dramatically more effective for removing heat stable salts from alkanolamine solutions than strongly acidic cationic exchange resins.

Specifically, it has been found in accordance with the invention that ion exchange resins are useful for purifying used aqueous alkanolamine solutions, in the following order of preference: Weak Acid IX > Weak Base IX > Strong Acid IX > Strong Base IX.

13 Claims, 1 Drawing Sheet

CLEAN UP OF ETHANOLAMINE SOLUTION BY TREATING WITH WEAK ION EXCHANGE RESINS

CROSS-REFERENCE TO RELATED APPLICATIONS

This is a continuation-in-part of U.S. application Ser. No. 628,310, filed Dec. 17, 1990, now abandoned, which is a continuation in part of U.S. application Ser. No. 542,282, filed Jun. 22, 1990 now abandoned, which is a continuation of U.S. application Ser. No. 288,392, filed Dec. 22, 1988 now abandoned, which is a division of U.S. application Ser. No. 113,316, filed Oct. 28, 1987, now U.S. Pat. No. 4,795,565.

FIELD OF THE INVENTION

The present invention relates generally to the field of gas purification. More specifically, the invention relates to the use of ethanolamine sorbents in hydrocarbon gas deacidification.

BACKGROUND OF THE INVENTION

Alkanolamine process units remove $H_2S$ and $CO_2$ from gaseous process streams, typically by countercurrently contacting an aqueous solution containing from about 20% to about 50% by weight of an alkanolamine with a gas stream containing $H_2S$ and/or $CO_2$. For the purpose of this application, it is understood that the terms "alkanolamine" and "ethanolamine" are generic terms including, but not limited to, monoethanolaminel diethanolamine, triethanolamine, and methyl diethanolamine.

The removal of hydrogen sulfide from gaseous streams, such as the waste gases liberated in the course of various chemical and industrial processes, for example, in wood pulping, natural gas and crude oil production and in petroleum refining, has become increasingly important in combating atmospheric pollution. Hydrogen sulfide containing gases not only have an offensive odor, but such gases may cause damage to vegetation, painted surfaces and wildlife, and further may constitute a significant health hazard to humans. Government-wide regulations have increasingly imposed lower tolerances on the content of hydrogen sulfide which can be vented to the atmosphere, and it is now imperative in many localities to remove virtually all the hydrogen sulfide under the penalty of an absolute ban on continuing operation of a plant or the like which produces the hydrogen sulfide-containing gaseous stream. Solutions of water and one or more the alkanolamines are widely used in industry to remove hydrogen sulfide and carbon dioxide from such gaseous streams.

Corrosion in alkanolamine units significantly increases both operating and maintenance costs. The mechanisms of corrosive attack include general corrosive thinning, corrosion-erosion, and stress-corrosion cracking. Corrosion control techniques include the use of more expensive corrosion and erosion resistant alloys, continuous or periodic removal of corrosion-promoting agents in suspended solids by filtration, activated carbon adsorption, or by the addition of corrosion inhibitors. (See Kohl, A. L. and Reisenfeld, F. C., *Gas Purification*, Gulf Publishing Company, Houston, 1979, pp. 91–105, as well as K. F. Butwell, D. J. Kubec and P. W. Sigmund, "Alkanolamine Treating", *Hydrocarbon Processing*, March, 1982.)

Further, it has been found that the acid gas sorption capacity in a circulating alkanolamine-water system decreases with time on stream in the absence of added makeup alkanolamine. This performance degradation has been found to be partially attributable to the accumulation of heat stable salts. U.S. Pat. No. 4,795,565 to Yan describes a process for removing heat stable salts from an ethanolamine system by the use of ion exchange resins. The disclosure of U.S. Pat. No. 4,795,565 to Yan is incorporated herein by reference for the operating details both of an ethanolamine acid gas sorption system as well as for the heat stable salt removal process.

Heat stable salts may also be removed from an alkanolamine system by distillation. However, such separation has been limited in the past to relatively mild conditions of temperature and pressure to avoid thermal degradation of the alkanolamine. For example, diethanolamine (DEA) boils at 268° C. at 760 mm Hg pressure and tends to oxidize and decompose at high temperature. For this reason, vacuum distillation has not been widely used to separate heat stable salts from spent alkanolamine solutions.

The Yan '565 patent cited above teaches that strongly acidic and basic cationic and anionic exchange resins are preferred to remove accumulated salts from ethanolamine solutions. See the Yan '565 patent at column 4, lines 4–61.

The chemistry of alkanolamine degradation is discussed in the Butwell et al. article cited above. Briefly, the Butwell et al. article notes that monoethanolamine (MEA) irreversibly degrades to N-(2-hydroxyethyl) ethylene diamine (HEED). HEED shows reduced acid gas removal properties and becomes corrosive at concentrations of at least about 0.4% by weight.

Diglycolamine (DGA), on the other hand, is said to produce a degradation product upon reaction with $CO_2$ which exhibits different properties. DGA, a registered trademark of Texaco, Inc., identifies an amine having the chemical formula $NH_2-C_2H_4-O-C_2H_4-OH$. DGA degrades in the presence of $CO_2$ to form N,N'-bis(hydroxyethoxyethyl) urea (BHEEU) which is similar to HEED in corrosivity but differs in that BHEEU has no acid gas removal properties.

Diethanolamine (DEA) reacts with $CO_2$ to form N,N'-di(2-hydroxyethyl) piperazine. Unlike HEED and BHEEU, the piperazine compound is noncorrosive and has acid gas removal properties essentially eclual to its parent, DEA. See the Butwell et al. article at page 113.

Diisopropylamine (DIPA) readily degrades in the contact with $CO_2$ to form 3-(2-hydroxypropyl) 5-methyl oxazolidone which shows essentially no acid gas removal properties. See the Butwell et al. article at page 113.

Numerous degradation products formed by the reaction of $H_2S$, or a mixture of $H_2S$ and $CO_2$ with diethanolamine have been reported from analyses of operating diethanolamine acid gas sorption processes and are shown below in Table 1.

TABLE 1
COMPOUNDS RESULTING FROM DEA DEGRADATION

| Name | Abbreviation | Structural formula |
|---|---|---|
| N,N-Bis (2-hydroxyethyl) piperazine | HEP | HO—$CH_2$—$CH_2$—N(—$CH_2$—$CH_2$—)(—$CH_2$—$CH_2$—)N—$CH_2$—$CH_2$—OH |
| N,N,N-tris (2-hydroxyethyl) ethylenediamine | THEED | (HO—$CH_2$—$CH_2$)$_2$N—$CH_2$—$CH_2$—NH—$CH_2$—$CH_2$—OH |
| Hydroxyethyl imidazolidone | HEI | Ring: $CH_2$—$CH_2$—N($CH_2$—$CH_2$—OH)—C(=O)—N(H?)—$CH_2$ |
| N-Methyldiethanolamine | MDEA | (HO—$CH_2$—$CH_2$)$_2$N—$CH_3$ |
| Oxazolidone | OZO | Ring: $CH_2$—N(H)—C(=O)—O—$CH_2$ |
| Aminoethylkethanolamine | AEEA | $NH_2$—$CH_2$—$CH_2$—NH—$CH_2$—$CH_2$—OH |
| Bis-(2-hydroxy ethyl) glycine | BHG | (HO—$CH_2$—$CH_2$)$_2$N—$CH_2$—C(=O)—OH |

The complex chemistry of alkanolamine degradation may account at least in part for the unpredictable behavior of ion exchange resins for removing heat stable salts from aqueous alkanolainine solutions.

SUMMARY OF THE INVENTION

The present invention provides a process for removing heat stable salts which accumulate in ethanolamine gas purification process units. Surprisingly, it has been found that weakly acidic cationic exchange resins are dramatically more effective for removing heat stable salts from ethanolamine solutions than strongly acidic cationic exchange resins. This result is indeed surprising, particularly in view of the teachings of the Yan '565 patent, which noted that strongly acidic sulfonic acid resins are more preferred for their greater stability. But now it has been found that the weakly acidic resins outperform the strongly acidic resins to an extent sufficient to prefer the weakly acidic resins, notwithstanding the required compromise in stability. Thus it has been found in accordance with the invention that ion exchange resins are useful for purifying used aqueous ethanolamine solutions, in the following order of preference:

Weak Acid IX > Weak Base IX > Strong Acid IX > Strong Base IX

Ethanolamine is most often used to purify hydrocarbon gases by removing $H_2S$ and $CO_2$. The ethanolamine is used as a 20–50% aqueous solution. The $H_2S$ and $CO_2$ in the hydrocarbon gas react with ethanolamine and are removed. While there are various ethanolamines, (such as monoethanolamine (MEA), diethanolamine (DEA) and triethanolamine (TEA) and methyl diethanolamine (MDEA)), which can be used in this process, it is preferred to employ the subject invention with an aqueous solution comprising an ethanolamine which boils at above 400° F. at atmospheric pressure. The choice of ethanolamine depends on the particular situations. For purification of natural gas with high $CO_2/H_2S$ ratio, diethanolamine is frequently the choice.

In the course of operation, some heat stable salts accumulate in the system. These include $SO_4^=$, $Cl^-$, $K^+$ and $Na^+$ as well as organic acid salts such as formates and acetates. It is known that these heat stable salts impair the performance and increase the corrosion rate of the ethanolamine unit.

In a monoethanolamine system, four ethanolamine solution purification techniques are commonly available to remove precipitates and heavy sludges: (1) settling, (2) filtration, (3) distillation and (4) activated carbon adsorption. While settling and filtration effectively remove solids from the alkanolamine solution, these techniques are ineffective to remove heat stable salts.

Distillation can be effective for purifying monoethanolamine solutions, but is less attractive for application to diethanolamine and triethanolamine systems due to temperature limitations. The temperatures required for the purification of DEA, TEA OR MDEA by distillation lead to thermal degradation of the amine. These undesired degradation products boil in a narrow range of temperatures around the boiling point of the associated amine, making separation by distillation extremely difficult. The problem of thermal degradation is somewhat less severe under vacuum distillation conditions.

Equipment and operating costs for vacuum distillation are generally higher than those associated with distillation under positive pressure. However, the costs are dramatically higher for diethanolamine regeneration facilities associated with natural gas purification, where the diethanolamine or monoethanolamine solution to be distilled must be depressored from in excess of about 700 psig to below atmospheric pressure, distilled under a vacuum, and then pumped back up to about 700 psig to reenter the ethanolamine gas purification system. Consequently, such purification by distillation is disfavored in industry.

In accordance with this invention, it has been found that the extraction of heat stable salts from aqueous alkanolamine solutions using certain ion-exchange resins can be carried out substantially independently of pressure. The present invention provides, in a first aspect, a process for rejuvenating a spent aqueous solution comprising the steps of:

(a) providing an aqueous alkanolamine solution having alkanolamine concentration sufficient to effectively sorb $H_2S$, $CO_2$, or both from a gaseous hydrocarbon stream having $H_2S$, $CO_2$, or both dissolved therein;

(b) continuously contacting said aqueous alkanolamine solution with said hydrocarbon gas stream of step (a) whereby salts are accumulated in said aqueous alkanolamine solution, said salts exerting a deleterious effect on the acid gas sorption capacity of said aqueous alkanolamine solution while increasing the corrosivity of said aqueous alkanolamine solution;

(c) contacting at least a portion of said aqueous alkanolamine solution of step (a) with a weak cationic exchange resin having a pKa of from about 1 to about 7, preferably from about 2 to about 6, for time sufficient to sorb from said aqueous alkanolamine solution at least a portion of said accumulated salts;

(d) repeating steps (b) and (c) to maintain the acid gas sorption capacity of said aqueous alkanolamine solution at a substantially constant value in the absence of fresh makeup ethanolamine.

The invention provides, in a second aspect, a process for purifying a hydrocarbon gas stream containing $H_2S$, $CO_2$, or both comprising the steps of:

(a) providing a hydrocarbon gas stream containing $H_2S$, $CO_2$, or both;

(b) contacting said hydrocarbon gas stream of step (a) with an aqueous ethanolamine solution having ethanolamine concentration sufficient to effectively sorb $H_2S$, $CO_2$, or both from said hydrocarbon gas stream of step (a);

(c) accumulating salts in said aqueous ethanolamine solution of step (b) to evolve a spent aqueous ethanolamine solution having decreased sorption affinity for $H_2S$, $CO_2$, or both;

(d) contacting said spent aqueous ethanolamine solution of step (c) with a weak cationic exchange resin having a pKa of from about 1 to about 7, preferably from about 2 to about 6 for time sufficient to at least partially purify said aqueous ethanolamine solution to provide an intermediate stream having greater acid gas sorption affinity than said spent aqueous ethanolamine solution of step (c);

(e) contacting said intermediate stream of step (d) with a weak anionic exchange resin characterized by pKa of from about 7 to about 14, preferably from about 8 to about 12, for time sufficient to sorb from said intermediate stream of step (d) at least a portion of said accumulated salts to form a purified aqueous ethanolamine solution having greater acid gas sorption affinity than said intermediate stream;

(f) recycling said purified aqueous ethanolamine solution of step (e) to said contacting step (b); and (g) continuously repeating steps (b) through (f).

The invention still further provides, in a third aspect, a continuous process for purifying a hydrocarbon gas stream containing $H_2S$, $CO_2$, or both comprising the steps of:

(a) providing a hydrocarbon gas stream containing $H_2S$, $CO_2$, or both;

(b) contacting said hydrocarbon gas stream of step (a) with an aqueous ethanolamine solution having ethanolamine concentration sufficient to effectively sorb $H_2S$, $CO_2$, or both from said hydrocarbon gas stream of step (a);

(c) accumulating salts in said aqueous ethanolamine solution of step (b) to evolve a spent aqueous ethanolamine solution having decreased sorption affinity for $H_2S$, $CO_2$, or both;

(d) contacting said spent aqueous ethanolamine solution of step (c) with a weak cationic exchange resin having a pKa of from about 1 to about 7, preferably from about 2 to about 6, for time sufficient to sorb from said aqueous alkanolamine solution at least a portion of said accumulated salts to form a purified aqueous ethanolamine solution having greater acid gas sorption affinity than said spent aqueous alkanolamine solution of step (c);

(e) recycling said purified aqueous ethanolamine solution of step (d) to said contacting step (b);

(f) repeating steps (b) through (e) until said weak cationic exchange resin is deactivated;

(g) regenerating said weak cationic exchange resin by contacting said weak cationic exchange resin aqueous solution containing at least one selected from the group consisting of $(NH_4)_2CO_3$, $NH_4HCO_3$ and $NH_4OH$; and (h) repeating steps (b) through (g) with said regenerated weak cationic exchange resin of step (g).

The invention still further provides, in a fourth aspect, method for mitigating the corrosivity of an aqueous ethanolamine solution comprising the steps of:

(a) providing an aqueous ethanolamine solution characterized by a first rate of corrosive attack, $R_1$, on A.S.T.M. 1018 carbon steel;

(b) circulating said aqueous ethanolamine solution of step (a) in contact with a hydrocarbon gas having $H_2S$, $CO_2$, or both dissolved therein to remove $H_2S$, $CO_2$, or both from said hydrocarbon gas thereby altering the composition of said aqueous ethanolamine solution to increase the rate of corrosive attack of said aqueous ethanolamine solution on A.S.T.M. 1018 carbon steel to a second rate of corrosive attack, $R_2$;

(c) withdrawing a portion of said circulating aqueous ethanolamine solution of step (b);

(d) contacting said withdrawn aqueous ethanolamine solution of step (c) with a weak cationic exchange resin having a pKa of from about 1 to about 7, preferably from about 2 to about 6, to evolve a rejuvenated aqueous ethanolamine solution exhibiting a third rate of corrosive attack on A.S.T.M. 1018 carbon steel, $R_3$, wherein $R_1 < R_3 > R_2$;

(e) continuously recycling said rejuvenated aqueous ethanolamine solution of step (d) to said circulating step (b).

In a preferred embodiment, the process of the invention treats a filtered slipstream comprising from about 4% to about 20% and then reinjects the rejuvenated alkanolamine solution for continuous acid gas sorption.

DETAILED DESCRIPTION

Figure 1:
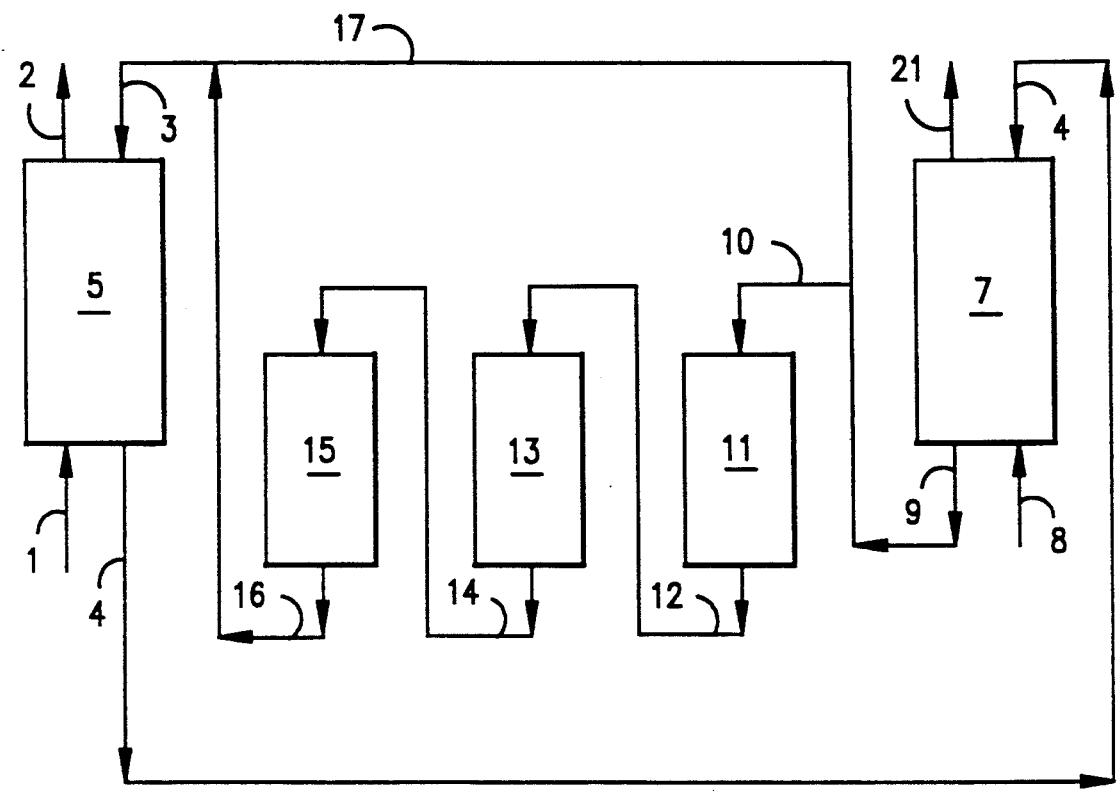
FIG. 1 is a simplified schematic diagram illustrating the major processing steps of one embodiment of the present invention.

Referring to FIG. 1, the crude gas 1 containing $CO_2$ and/or $H_2S$ is passed upwardly through the ethanolamine absorber column 5, where the crude gas is countercurrently contacted with lean ethanolamine solution 3. The lean ethanolamine solution 3 absorbs the $CO_2$ and $H_2S$, thereby purifying the gas. The purified gas stream 2 exits the top of the ethanolamine absorber column 5. Upon absorption of $CO_2$ and $H_2S$, the lean ethanolamine solution 3 becomes a rich ethanolamine solution 4.

The rich ethanolamine 4 is charged to the top of a stripper tower 7 and is stripped with steam 8 at about 240° F. to remove the $CO_2$ and $H_2S$ 21. Upon stripping, the rich ethanolamine 4 becomes lean ethanolamine 9. The lean ethanolamine 9 exits the bottom of the steam stripper tower 7 and is returned to the absorber 5 to start another cycle of absorption/stripping. However, a fraction of the lean ethanolamine 10 is passed through a filter medium 11 to remove the solid suspension. The filter may comprise any suitable configuration, examples of which include sock filters, PECO filters and activated charcoal filters. Of these, activated charcoal filters are preferred. The filtered stream 12 is fed to a second vessel 13 containing weakly basic anionic resins to remove anionic species, such as $SO_4^=$ and $Cl^-$. The effluent stream 14 then flows to a vessel containing weak cationic resins 15 to remove cations such as $Na^+$, $K^+$, and $Ca^{++}$. This cleaned lean ethanolamine solution 16 is combined with lean ethanolamine 17 to become the lean ethanolamine feed stream 3 for the ethanolamine absorber 5. In a separate operation, the ion exchange resins are regenerated from time to time for reuse.

The ion exchange resin aqueous regeneration solution comprises at least one of $(NH_4)_2CO_3$, $NH_4HCO_3$ and $NH_4OH$. These regenerants are particularly useful for regenerating weak cationic and anionic exchange resins in the present invention because the exchanged ions can be readily stripped from the circulating alkanolamine solution after the alkanolamine solution circulates through the freshly regenerated ion exchange resin. The effectiveness of these regenerants further highlights the distinction between strong and weak ion exchange resins, specifically that the regenerants listed above perform more efficiently with weak ion exchange resins than with strong ion exchange resins.

Figure 2:
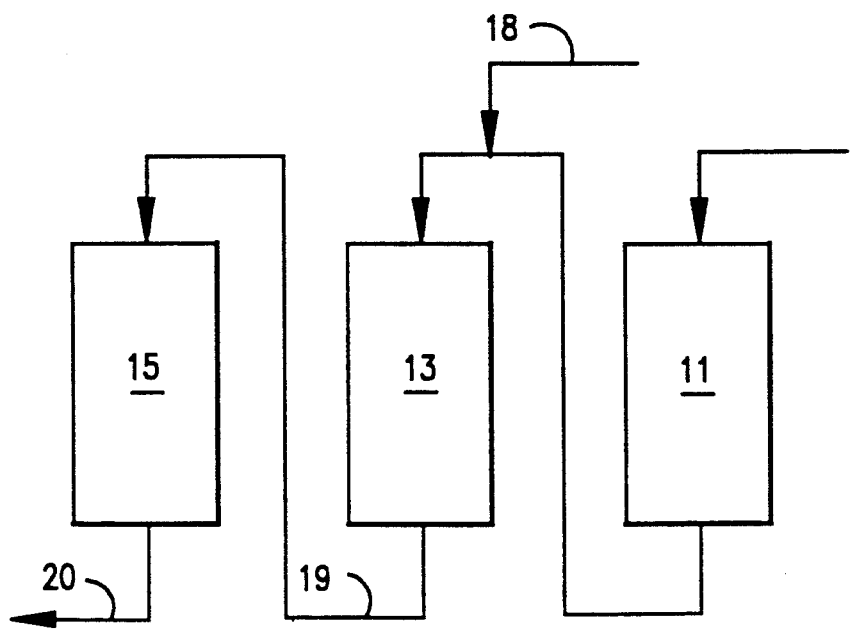
FIG. 2 is a simplified schematic diagram illustrating the major steps of the continuous process of the invention including the regeneration steps.

Turning now to FIG. 2, the regeneration solution comprising an aqueous solution of $(NH_4)_2CO_3$, $NH_4HCO_3$, $NH_4OH$ or a mixture thereof 18 is fed to the anionic ion-exchange vessel 13. The effluent 19 is fed to the cationic ion-exchange vessel 15. The effluent liquid 20 may then be disposed of or stripped with steam for reuse.

The fraction of lean ethanolamine which should be cleaned through the ion exchange varies with the extent of contamination. It can range between 0 and 100%, but 4–20% is preferred. It should be pointed out that this clean up loop should be operated continuously to ensure smooth operation. However, it can be operated intermittently. For example, the clean up loop can be shut down during the regeneration of the anionic or cationic resins and/or during filter change over.

While it is preferred for the anionic resins to precede the cationic resins in the cleanup loop, it should be understood that the reverse order will also achieve the desired result. Because regenerants such as $NH_4HCO_3$, $NH_4OH$ and $(NH_4)CO_3$ are used with the weak ion exchange resins in the present invention, the resins may be contained in separate vessels or optionally in separate beds in a single vessel.

The Anionic Exchange Resin

The weak anionic exchange resins useful in the present invention are characterized by pKa values of from about 7 to about 14 preferably from about 8 to about 12. These weak anionic exchange resins may be further characterized by their matrix structures, which include polystyrenes, epoxy-amines, phenolics, and condensates. Examples of suitable weak anionic exchange resins include those identified by the following tradenames: Allassion A33-03, Amberlite IRA-45, Amberlite IRA-93, De-Acidite G, De-Acidite M, Dowex 3, Imac A-20, Imac A-21, Ionac A-315, Lewatit MP-60, Allassion AWB-3, Anionite EDE-10P, Anionite AV-16, Dowex 44, Duolite A-30B, Duolite A-57, Imac, Ionac A-300, Ionac A-310, Wofatit L-150, Anionite AN-2F, De-Acidite E, Duolite A-6, Duolite A-7, Lewatit MIH 59 and Wofatit MD. For a survey of the chemistry of these useful weak ion exchange resins, see Irving L. Abrams and L. Benezra "Ion Exchange Polymers" 7 *Encyclopedia of Polymer Science and Technology* 706, (1967).

The Cationic Exchange Resin

The weak cationic exchange resins useful in the present invention are characterized by pKa values of from about 1 to about 7, preferably from about 2 to about 6. Most of the cationic exchange resins useful in the invention contain carboxylic acid groups, although weak cationic resins containing phenolic acid derivatives are also useful. For a survey of the chemistry of suitable weak cation exchange resins, see Irving L. Abrams and L. Benezra "Ion Exchange Polymers" 7 *Encyclopedia of Polmer Science and Technology* 704, (1967). Examples of suitable weak cationic exchange resins include those identified by the following tradenames: Allassion CC, Amberlite IRC-50, Amberlite IRC-84, Dowex CCR-1, Duolite ES-63, Duolite ES-80, Duolite CS-100, Duolite CS-101, Imac Z-5, Ionac C-270, Kastel C-100, Lewatit CNO, Wofatif CP-300, Wofatit CN, Zeo-Karb 216, and Zeo-Karb 226.

In a preferred embodiment, the anionic exchange resin is followed by the cationic exchange resin. The exchange resins may be contained in separate vessels or in a single mixed bed vessel. While it is preferred to arrange the exchange resins in series with the cationic exchange resin following the anionic exchange resin, the resins may also be placed in series with the anionic exchange resin following the cationic exchange resin.

The mixed bed in a single vessel is made up of two zones, in series, each containing a different type of ion exchange resin, for example, anionic exchange resin followed by cationic exchange resin.

The relative amount of anionic and cationic exchange resins required is calculated as follows:

$$R = \frac{\text{Anionic IX, g}}{\text{Cationic IX, g}}$$

$$= \frac{\text{Anionic Impurities in the Solution, mmol/liter}}{\text{Cationic Impurities in the Solution, mmol/liter}} \times \frac{\text{Capacity of Cationic IX, meq/g}}{\text{Capacity of Anionic IX, meq/g}}$$

Typically, the range of values for R is between about 1 and about 1.2.

In accordance with the invention, it has been discovered that $(NH_4)_2CO_3$, $NH_4HCO_3$, $NH_4OH$ and their mixtures can be used to regenerate both the anionic and cationic exchange resins in series. The regeneration solution is thus passed over the anionic resins and then over the cationic resins in the same order as the lean ethanolamine solution passes through the system during normal unit operation. Most importantly, the counter ions remaining in the ion exchange resins after regeneration, namely, $CO_3^=$ in the anionic and $NH_4^+$ in the cationic, will be removed by exchange with the impurities in the ethanolamine-water stream. The counter ions will then be stripped out of the ethanolamine solution downstream in the ethanolamine unit's stripper tower. Thus the ion exchange resins may be put back into service immediately following regeneration without further treatment. This i-S advantageous both from the economic and environmental points of view. The total concentrations of $(NH_4)_2CO_3$, $NH_4HCO_3$ and $NH_4OH$ can be 0.1 to 5 moles per liter, preferably 0.5 to 2 moles per liter.

EXAMPLES

A used aqueous DEA solution was withdrawn from an operating commercial acid gas sorption process. Analysis showed the DEA solution to contain approximately 45% organics and 55% water by weight. DEA and BHEP comprised 88.14% and 1.7% (weight), respectively, of the organics. The balance of the organics, 10.16% (weight) comprised several unidentified compounds.

The three resins which were evaluated are listed below.

Example 2

MSA-1

A strong anion exchange resin in the quaternary amine form, manufactured by the Dow Chemical Company of Midland, Mich.

Example 3

IONAC CC

A weak cation exchange resin, manufactured by Ionac Chemical Company, a division of Sybron Corporation of Birmingham, N.J., is the hydrogen form of a carboxylic acid, prepared by hydrolyzing the copolymer of polyacrylic acid and divinylbenzene.

Example 4

IONAC A-380

A strong cation exchange resin, manufactured by the Ionac Chemical Company, is the free form of tertiary amine, and a polyamine functionalized copolymer of polyacrylates.

Experimental Procedure

Aliquots (about 40 grams) of the resins were washed with deionized water and treated with excess $(NH_4)_2CO_3$. The treated resin was washed with water and then added to a 4 oz. jar containing about 120 grams of the used aqueous DEA solution described above. This slurry was then placed on a mixing roller. After about 4 hours of mixing, the aqueous DEA solution was decanted and tested for composition and corrosivity.

To determine corrosivity, the decanted aqueous DEA test solution was loaded with 0.5 mols $H_2S$ per mole of DEA and placed in a stainless steel bomb equipped with a standard ASTM C1018 carbon steel corrosion coupon of the type customarily used to determine corrosion rate in commercial DEA process units. The bomb was sealed, heated to 240° F., and maintained at elevated temperature for about 10 days. Corrosion rates were then determined from coupon weight loss, as shown below in Table 2. Corrosion rate is expressed in units of "mpy" or mils per year. As used herein, one (1) mil is equal to 0.001 inch.

TABLE 2

| Corrosion Testing Coupon: C1018 Carbon Steel Temperature: 240° C. $H_2S$ Loading: 0.5 mols/mol DEA | | |
|---|---|---|
| Solution Description | Days in Test | Corrosion Rate (mpy) |
| Example (1) Used Commercial DEA Solution (Control) | 9.8 | 7.6 |
| Example (2) Solution of Example (1) treated with resin MSA-I | 10.8 | 7.8 |
| Example (3) Solution of Example (1) treated with resin IONAC CC | 10.0 | 0.3 |
| Example (4) Solution of Example (1) treated with IONAC A380 | 10.0 | 2.8 |

Corrosion rate fell precipitously when the diethanolamine solution was treated with a weak cation exchange resin in Example 3. The effectiveness of the weak cation exchange resin (Example 3) in reducing corrosion rate exceeded that of the strong cation exchange resin (Example 4) by a factor greater than 9. Further, the weak cation exchange resin outperformed the strong anion exchange resin (Example 2) by a factor of 26 (0.3 mpy vs. 7.8 mpy).

Changes and modifications in the specifically described embodiments can be carried out without departing from the scope of the invention which is intended to be limited only by the scope of the appended claims.

What is claimed is:

1. A process for rejuvenating a spent aqueous alkanolamine solution comprising the steps of:
   (a) providing an aqueous alkanolamine solution having alkanolamine concentration sufficient to effectively sorb $H_2S$, $CO_2$, or both from a gaseous hydrocarbon stream having H$_2$S, CO$_2$, or both dissolved therein;

(b) continuously contacting said aqueous alkanolamine solution with said hydrocarbon gas stream of step (a) whereby salts are accumulated in said aqueous alkanolamine solution, said salts exerting a deleterious effect on the acid gas sorption capacity of said aqueous alkanolamine solution;

(c) contacting said aqueous alkanolamine solution of step (b) with a weak cationic exchange resin having a pKa of from about 1 to about 7 for time sufficient to sorb from said aqueous alkanolamine solution at least a portion of said accumulated salts;

(d) repeating steps (b) and (c) to maintain the acid gas sorption capacity of said aqueous alkanolamine solution at a substantially constant value in the absence of fresh makeup alkanolamine;

(e) regenerating said weak cationic exchange resins with an aqueous solution of (NH$_4$)$_2$CO$_3$, NH$_4$HCO$_3$, NH$_4$OH or a mixture thereof; and (f) removing counter-ions introduced by said regeneration solution by stripping said aqueous alkanolamine solution with steam and recycling said steam-stripped alkanolamine solution to step (b), wherein the corrosion rate in the presence of carbon steel is less than the same process using other ion exchange resins.

2. The process of claim 1 wherein said weak cation exchange resin of step (c) has a pKa of from about 2 to about 6.

3. The process of claim 1 wherein step (c) further comprises contacting a slipstream of said alkanolamine solution of step (b) with said weak cationic exchange resin and returning said slipstream to said hydrocarbon gas contacting step (a).

4. The process of claim 1 wherein said alkanolamine comprises at least one selected from the group consisting of monoethanolamine, diethanolamine, triethanolamine, and methyl diethanolamine.

5. A process for purifying a hydrocarbon gas stream containing H$_2$S, CO$_2$, or both comprising the steps of:

(a) providing a hydrocarbon gas stream containing H$_2$S, CO$_2$, or both;

(b) contacting said hydrocarbon gas stream of step (a) with an aqueous alkanolamine solution having alkanolamine concentration sufficient to effectively sorb H$_2$C, CO$_2$, or both from said hydrocarbon gas stream of step (a);

(c) accumulating salts in said aqueous alkanolamine solution of step (b) to evolve a spent aqueous alkanolamine solution having decreased sorption affinity for H$_2$S, CO$_2$, or both;

(d) contacting said spent aqueous alkanolamine solution of step (c) with a weak cationic exchange resin having a pKa of from about 1 to about 7 for time sufficient to at least partially purify said aqueous alkanolamine solution to provide an intermediate stream having greater acid gas sorption affinity than said spent aqueous alkanolamine solution of step (c);

(e) contacting said intermediate stream of step (d) with a weak anionic exchange resin having a pKa of from about 7 to about 14 for time sufficient to sorb from said intermediate stream of step (d) at least a portion of said accumulated salts to form a purified aqueous alkanolamine solution having greater acid gas sorption affinity than said intermediate stream of step (d);

(f) recycling said purified aqueous alkanolamine solution of step (e) to said contacting step (b);

(g) regenerating said weak cationic exchange resin and said weak anionic exchange resin with an aqueous regeneration solution of (NH$_4$)$_2$CO$_3$, NH$_4$HCO$_3$, NH$_4$OH, or a mixture thereof;

(h) continuously repeating steps (b) through (g); and (i) removing counter-ions introduced by said generation solution by stripping said aqueous alkanolamine solution with steam and recycling said steam-stripped alkanolamine solution to step (b), wherein the corrosion rate in the presence of carbon steel is less than the same process using other ion exchange resins.

6. The process of claim 5 wherein said weak cationic exchange resin of step (d) has a pKa of from about 2 to about 6 and said weak anionic exchange resin has a pKa of from about 8 to about 12.

7. The process of claim 5 further comprising filtering said spent alkanolamine solution of step (c) to remove particulates.

8. The process of claim 5 wherein step (d) further comprises contacting a slipstream of said spent alkanolamine solution of step (c) with said weak cationic exchange resin of step (d).

9. The process of claim 8 wherein said slipstream comprises from about 4 to about 20 percent of the total flow of said alkanolamine solution.

10. The process of claim 9 wherein said alkanolamine is at least one selected from the group consisting of monoethanolanine, diethanolamine, triethanolamine, and methyl diethanolamine.

11. The process of claim 10 wherein said alkanolamine is diethanolamine.

12. A continuous process for purifying a hydrocarbon gas stream containing H$_2$S, CO$_2$, or both comprising the steps of:

(a) providing a hydrocarbon gas stream containing H$_2$S, CO$_2$, or both;

(b) contacting said hydrocarbon gas stream of step (a) with an aqueous diethanolamine solution having diethanolanine concentration sufficient to effectively sorb H$_2$S, CO$_2$, or both from said hydrocarbon gas stream of step (a);

(c) accumulating salts in said aqueous diethanolamine solution of step (b) to evolve a spent aqueous diethanolamine solution having decreased sorption affinity for H$_2$S, CO$_2$, or both;

(d) contacting said spent aqueous diethanolamine solution of step (c) with a weak cationic exchange resin having a pKa of from about 1 to about 7 for time sufficient to sorb from said aqueous diethanolamine solution at least a portion of said accumulated salts to form a purified aqueous diethanolamine solution having greater acid gas sorption affinity than said spent aqueous diethanolamine solution of step (c);

(e) recycling said purified aqueous diethanolamine solution of step (d) to said contacting step (b);

(f) repeating steps (b) through (e) until said weak cationic exchange resin is deactivated;

(g) regenerating said weak cationic exchange resin by contacting said weak cationic exchange resin aqueous solution containing at least one selected from the group consisting of (NH$_4$)$_2$CO$_3$, NH$_4$HCO$_3$ and NH$_4$OH; and (h) repeating steps (b) through (g) with said regenerated weak cationic exchange resin of step (g), wherein the corrosion rate in the presence of carbon steel is less than the same process using other ion exchange resins.

13. A method for mitigating the corrosivity of an aqueous diethanolamine solution comprising the steps of:
  (a) providing an aqueous diethanolamine solution characterized by a first rate of corrosive attack, $R_1$, on A.S.T.M. 1018 carbon steel;
  (b) circulating said aqueous diethanolamine solution of step (a) in contact with a hydrocarbon gas having $H_2S$, $CO_2$, or both dissolved therein to remove $H_2S$, $CO_2$, or both from said hydrocarbon gas thereby altering the composition of said aqueous diethanolamine solution to increase the rate of corrosive attack of said aqueous diethanolamine solution on A.S.T.M. 1018 carbon steel to a second rate of corrosive attack, $R_2$;
  (c) withdrawing a portion of said circulating aqueous diethanolamine solution of step (b);
  (d) contacting said withdrawn aqueous diethanolamine solution of step (c) with a weak cationic exchange resin having a pKa of from about 2 to about 6 to evolve a rejuvenated aqueous diethanolamine solution exhibiting a third rate of corrosive attack on A.S.T.M. 1018 carbon steel, $R_3$, wherein $R_1 < R_3 < R_2$;
  (e) continuously recycling said rejuvenated aqueous diethanolamine solution of step (d) to said circulating step (b).
  (f) repeating steps (b) through (e) until said weak cationic exchange resin is deactivated;
  (g) regenerating said weak cationic exchange resin by contacting said weak cationic exchange resin aqueous solution containing at least one selected from the group consisting of $(NH_4)_2CO_3$, $NH_4HCO_3$ and $NH_4OH$; and
  (h) repeating steps (b) through (g) with said regenerated weak cationic exchange resin of step (g), wherein the corrosion rate in the presence of carbon steel is less than the same process using other ion exchange resins.

* * * * *